(12) United States Patent
Pitochelli

(10) Patent No.: US 6,197,215 B1
(45) Date of Patent: Mar. 6, 2001

(54) COMPOSITION FOR GENERATING CHLORINE DIOXIDE

(75) Inventor: Anthony R. Pitochelli, Witchita, KS (US)

(73) Assignee: Vulcan Chemicals, Birmingham, AL (US)

(*) Notice: Subject to any disclaimer, the term of this patent is extended or adjusted under 35 U.S.C. 154(b) by 0 days.

(21) Appl. No.: 09/257,627

(22) Filed: Feb. 25, 1999

(51) Int. Cl.$^7$ .................. A01N 59/08; A61K 33/14; A62D 3/00; C01B 7/00
(52) U.S. Cl. .................. 252/187.21; 252/186.1; 252/187.1; 252/187.23; 252/187.24; 252/187.25; 252/187.26; 252/187.27; 252/187.28; 252/187.29; 252/187.3; 424/661
(58) Field of Search .................. 252/186.1, 187.1, 252/187.21, 187.23–187.3, 187.24, 187.25; 424/661

(56) References Cited

U.S. PATENT DOCUMENTS

| | | |
|---|---|---|
| 4,104,190 | 8/1978 | Hartshorn . |
| 4,689,169 | 8/1987 | Mason et al. . |
| 5,399,288 | 3/1995 | Marzouk et al. . |
| 5,472,715 | 12/1995 | Uehara . |
| 5,736,165 | 4/1998 | Ripley et al. . |

FOREIGN PATENT DOCUMENTS 2 304 706 * 3/1997 (GB) .

* cited by examiner

*Primary Examiner*—Jill Warden
*Assistant Examiner*—Monique T. Cole
(74) *Attorney, Agent, or Firm*—Leonard Bloom

(57) ABSTRACT

A dry disinfectant composition for the production of aqueous solutions of chlorine dioxide is formulated of a mixture of lithium hypochlorite, sodium bisulfate and sodium chlorite.

12 Claims, 1 Drawing Sheet

COMPOSITION FOR GENERATING CHLORINE DIOXIDE

FIELD OF THE INVENTION

The invention finds applicability in fields where chlorine dioxide is generally used and particularly in the fields of disinfection and odor treatment and demand studies.

BACKGROUND OF THE INVENTION

The inventor has been working on developing solid mix formulations which will allow the preparation of small quantities (normally one liter, but the same mix can be used to prepare up to 300 gallons or more) of an aqueous chlorine dioxide solution at repeatable and reproducible concentration of up to and beyond 3000 mg/l.

Prior Art Patents

The chemistry for producing chlorine dioxide is well known and has been the subject of at least two patents, U.S. Pat. No. 5,399,288 and U.S. Pat. No. 4,104,190.

Marzouk et al in U.S. Pat. No. 5,399,288 teaches solid chlorine dioxide releasing compositions involving the use of a triazinetrione.

Hartshorn in U.S. Pat. No. 4,104,190 discloses a dry composition for releasing chlorine dioxide containing dichloroisocyanurate as the chlorine releasing compound.

The prior art does not teach lithium hypochlorite in chlorine dioxide releasing compositions as taught by the herein disclosed invention.

Chlorine dioxide is a powerful, selective oxidant which finds use as a drinking water disinfectant, in cooling tower bilogical control, as a paper pulp bleach, a disinfectant in fruit, vegetable and poultry processing, for oil well and water injection well stimulation, in wastewater treatment, as an algaecide, and as an odor control agent. Almost all applications use gaseous chlorine dioxide as a dilute aqueous solution, usually at or below 3000 ppm. This solution cannot be supplied to the end user ready for use. Aside from the unattractive economics of shipping a solution which is 99.7% water, shipment is forbidden by the DOT. Unlike liquefied chlorine, the condensed liquefied gas cannot be prepared and shipped in cylinders because of its extreme shock sensitivity. As a consequence, it is necessary that chlorine dioxide be prepared on site at the time of use by combining the appropriate precursors in a chlorine dioxide generator. These precursors include aqueous solutions of sodium chlorate or sodium chlorite, mineral or organic acids, chlorine, sodium hypochlorite, or some combination of these, usually as aqueous solutions which are metered out in the appropriate amounts and combined under controlled conditions by the chlorine dioxide generator. The need for a generator has usually limited use of this oxidant to those situations which justified the expense of installing and maintaining the necessary equipment. Typically, the smallest generators commercially available make 30 pounds per day of gaseous chlorine dioxide. This invention allows the use of chlorine dioxide treatment in those situations where the product's unique capabilities are attractive, but which are too small to justify installation and use of a generator.

OBJECTS OF THIS INVENTION

The inventor expects there to be strong consumer interest in using non-toxic, inorganic dry mix packets to prepare chlorine dioxide and particularly for disinfecting drinking water. The inventor's intent is that the composition be employed both for short term use, such as, for preparing emergency drinking water, and for treating drinking water for daily consumption.

An important object of this invention is to provide a disinfecting composition without there being organic material being present.

The herein disclosed invention has for an object providing a convenient way to prepare small quantities of chlorine dioxide which are safe for treating drinking water or for disinfecting fruits and vegetables and like products.

Another object of this invention is to produce a product which will give consistent results for disinfecting drinking water and especially poor quality drinking water which might be available in emergency situations.

A further object of this invention is to produce a product which is non-toxic when used as directed.

A major object of this invention is to produce a dry mix formulation which produces hypochlorous acid precursor on addition of water to the dry mix and which does not introduce objectionable organic by-products.

A critical part of this invention is the incorporation in the mix of a component which rapidly generates hypochlorous acid on contact with water. The inventor has developed a formulation suitable for the disinfection of drinking water. The new formulation contains three components: lithium hypochlorite, sodium bisulfate and sodium chlorite. The inventor has found that when these three solids in various quantities are added to a suitable quantity of water, the solids dissolve completely within 45 seconds, and at the end of this brief period, have generated as much chlorine dioxide as the mix will form. The system generates chlorine above its solubility in water, and so the gas bubbles generated agitate the mixture and speed up reaction and solution of components. The rapidity of solution is surprising.

These and other objects of the present invention will become apparent from a reading of the following specification taken in conjunction with the enclosed drawing.

BRIEF SUMMARY OF THE INVENTION

The dry mix formulation which is the heart of this invention incorporates lithium hypochlorite, 25–30 weight % LiOCl; sodium hydrogen sulfate (synonym: sodium bisulfate), $NaHSO_4$; and 80% dry solid sodium chlorite, $NaClO_2$.

Regarding the $LiOCl_2$ 25–30 wt %, the composition used in this invention is:

| COMPONENT | WT % |
|---|---|
| Lithium Hypochlorite | 25–30 |
| Sodium Chloride | 36 |
| Sodium Sulfate | 13 |
| Potassium Sulfate | 6 |
| Lithium Chloride | 4 |
| Lithium Carbonate | 2 |
| Lithium Chlorate | 2 |
| Lithium Hydroxide | 1 |
| Water | 7 |

The ingredients other than the lithium hypochlorite were inert and are not necessary to the performance of this invention. These inert components could be substituted with other inert compatible salts or the like as would be understood by those skilled in the art. A product providing the above formulation can be obtained from FMC Corporation or could be readily formulated by those skilled in the art.

The 80% dry solid sodium chlorite product employed in the examples of this invention is as follows:

| COMPONENT | SPECIFICATIONS |
|---|---|
| Sodium Chlorite, wt % as $NaClO_2$ | 77.5–82.5 |
| Sodium Chlorate, wt % as $NaClO_3$ | 4 max. |
| Sodium Chloride, wt % as NaCl | 11–19 |
| Sodium Hydroxide, wt % as NaOH | 3 max. |
| Sodium Carbonate, wt % as $Na_2CO_3$ | 2 max. |
| Sodium Sulfate, wt % as $Na_2SO_4$ | 3 max. |
| Hydrogen Peroxide, wt % as $H_2O_2$ | 0.01 max. |
| Water (by difference), wt % | 6 max. |

It is to be understood that the main active ingredient is the Sodium Chlorite and the other components are ancillary thereto and are deemed to be inert. These inert ingredients are not essential to the invention and could be replaced by other like inert ingredients as readily understood by those skilled in the art.

In its preferred embodiment, the lithium hypochlorite and sodium bisulfate are packaged together in one pouch or container, and the sodium chlorite is packed separately in another pouch or container which may or may not be connected. This two-packet system has two purposes; one is to improve storage stability, especially under conditions of elevated temperature. The other purpose is to allow the components to be mixed in a prescribed manner to ensure a specific known, final concentration of generated chlorine dioxide. A single packet containing a stable mix of all three components is also possible, but this single packet must be maintained at a temperature below 140° F. (preferably below 125° F.) to avoid decomposition. This single mix has a further disadvantage of generating chlorine dioxide of variable and unpredictable concentrations as a function of variations in the method of mixing (See FIG. 1).

A solid mix has been devised which rapidly generates chlorine dioxide when added to water. The mix will allow the generation of a known quantity of aqueous chlorine dioxide in a predictable concentration to be used for the disinfection of drinking water, fruits and vegetables, biocidal treatment of cooling towers, treatment of medical waste and other disinfection, and most especially industrial applications, which are too small to justify the installation of a chlorine dioxide generator. The mix can also be used for small scale odor control.

Properly formulated, the three component mixture of this invention can be used to disinfect fruits and vegetables at a concentration of chlorine dioxide in water as low as 1–2 ppm. A concentration of about 100 ppm would be operative for use as a deodorant.

The separated two-pack products of this invention have been found to be thermally stable in tests performed to a temperature of above 140° F.

Figure 1:
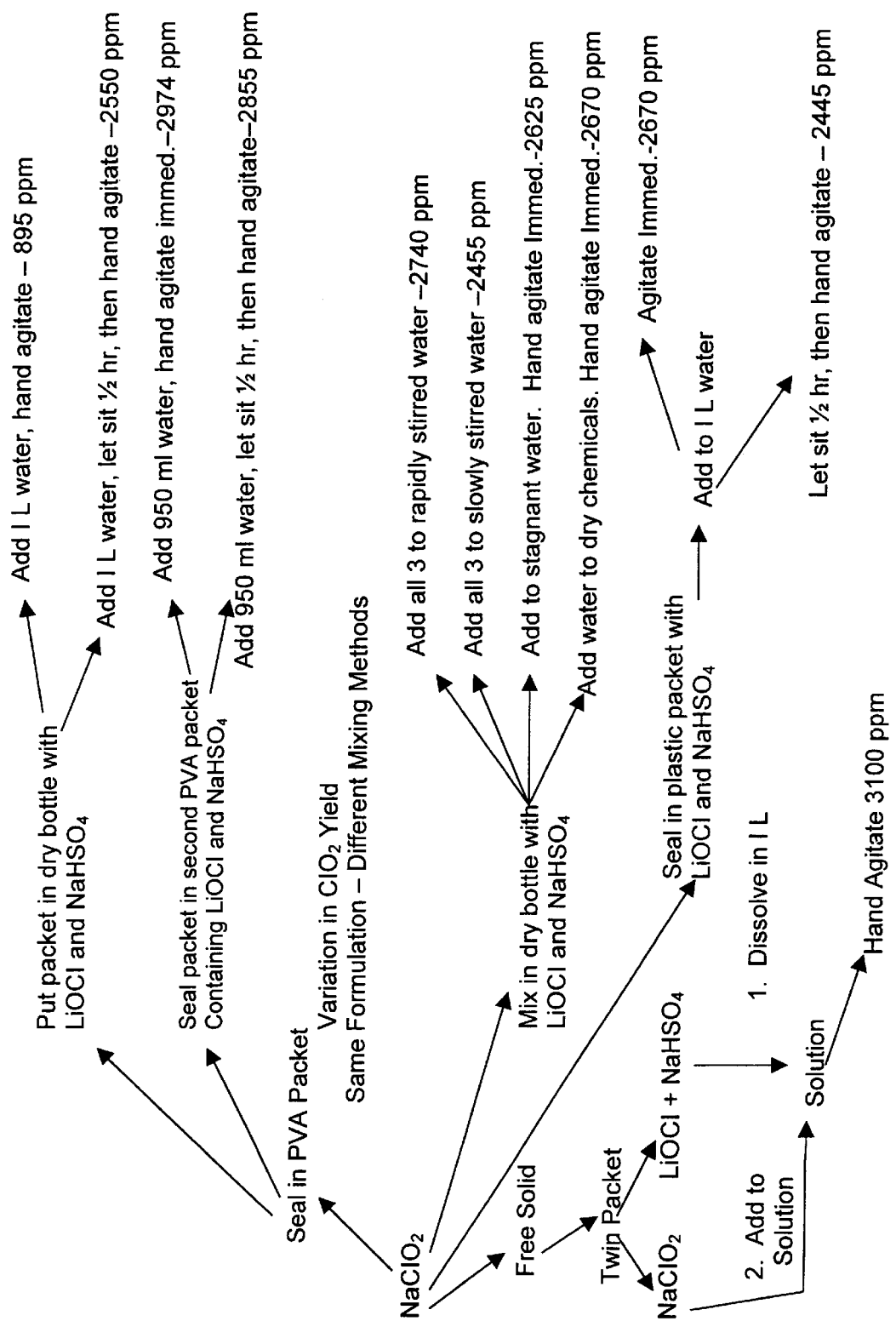
With reference to FIG. 1, a diagram shows variation of $ClO_2$ yield depending upon the method of mixing. In all of the tests shown in FIG. 1, the formulations were of the same amounts differing only in the method of mixing.

Part of the art of this invention involves the manner of mixing the components. As the attached chart (FIG. 1) shows, different types of mixes containing the exact same quantities of each of the components will give chlorine dioxide solutions of differing concentrations depending on how the components are mixed with water. It is an intent of this invention to formulate a product which allows a user in the field to prepare a solution of chlorine dioxide of known and desired concentration predictably and reliably, so that a dosage rate can be selected and the chlorine dioxide applied without the need for chlorine dioxide assay.

In one embodiment of the invention, the inventor intends to provide packages of the disinfectant formulations in water soluble packets for ease of use. In that way, instead of having to empty the contents of a packet in water, the entire soluble packet and/or packets and their contents can be placed in water to be treated.

As a matter of convenience, a mix has been devised which can reliably give one liter of 3000 ppm chlorine dioxide when the components are combined with water in a specified manner. This mix is provided in packs called an Activator Packet and a Chlorite Packet:

Activator Packet contains:
LiOCl (25–30 weight %): 6.12 g and
$NaHSO_4$ 7.7 g
Chlorite Packet contains:
80% $NaClO_2$: 5.6 g With the LiOCl and the $NaClO_2$, the balance of the product is an inert ingredient.

When the Activator Packet and the Chlorite Packet are properly added to a liter of water, substantially 3000 ppm of chlorine dioxide will be produced.

Component ratios based on chlorite are approximately:
$NaClO_2$=1.0 (80 weight percent)
LiOCl=1.09 (25–30 weight percent)
$NaHSO_4$=1.38

It should be understood that the invention is not limited to compositions which generate only one liter of solution, but can be adjusted to produce any volume less than or more than one liter. While the actual weight of each component will be apportioned depending on the intended volume of final solution, the ratio of components must be maintained to ensure efficient chlorite conversion and the best yield and purity of chlorine dioxide.

It should also be understood that the selection of a chlorine dioxide concentration of 3000 ppm is arbitrary, and that solutions substantially below and above this concentration are possible. Solutions in excess of 5000 ppm have been prepared with properly formulated mixtures of components. Generation of very dilute solutions (1–100 ppm) is possible by using very small quantities of each of the reactants, however, to ensure rapid, complete and accurate chlorite conversion, it is preferred that a more concentrated solution be prepared and subsequently diluted to the desired concentration.

It is to be understood that if an exact final concentration of chlorine dioxide is not required, lithium hypochlorite, sodium bisulfate and sodium chlorite in substantial amounts as taught by this invention can be used.

The user has the flexibility in combining the Activator Packet and the Chlorite Packet with the appropriate volume of water in any manner he chooses, however in order to ensure that the concentration of the final solution be as intended, the packets must be used in a prescribed manner, namely, complete dissolution of the Activator Packet, which requires less than one minute, and then the addition and rapid complete solution of the Chlorite Packet. When the chlorite is completely dissolved, the solution is at full strength and ready to be used. It is necessary to use this two-step method in combination in order to ensure that prior to the addition of chlorite, the lithium hypochlorite has been completely converted to hypochlorous acid by reaction with the acid produced on solution and hydrolysis of the sodium bisulfate. Hypochlorous acid reacts rapidly with chlorite anion to give high yields of chlorine dioxide. If, instead of the adding the components sequentially as required, the chlorite is simultaneously combined with activator, either by adding both packets of the two packet system, or by adding the single packet of the one packet system, a competitive reaction between hypochlorite anion and chlorite anion occurs which converts some of the chlorite to inert chlorate, reducing the quantity of chlorite available for conversion and, thereby, reducing the yield of chlorine dioxide. If directions as to how the components are mixed or agitated are not followed, a chlorine dioxide solution of unpredictable concentration is prepared, robbing the invention of an important part of its value, namely, that of producing a chlorine dioxide solution of predictable concentration, eliminating the need for field assay prior to use and allowing the end user to apply chorine dioxide at the correct dosage rate intended.

As referred to earlier, in addition to the two-packet system, all three components can also be combined into a stable mix in a single packet. This mix is somewhat more thermally sensitive than the two-packet system, but nevertheless is stable if kept below 140° F. On addition of this one pack formulation embodiment to water, it is impossible to avoid the competitive reaction between hypochlorite anion and chlorite anion which generates chlorate and depletes chlorite. When using the one pack formulation, it is necessary to adjust the quantities and ratios of the components to allow for some hypochlorite and chlorite loss. The component quantities and ratios for the one packet formulation are:

| LiOCl 25–30 weight %: | 6.16 g |
|---|---|
| NaHSO$_4$: | 7.7 g |
| NaClO$_2$ (80 weight %): | 6.33 g |

The ratios, based on chlorite are:

| NaClO$_2$ = 1.0 |
|---|
| LiOCl = 0.97 |
| NaHSO$_4$ = 1.22 |

While this single packet system offers improved convenience over the two packet system, it is not the preferred embodiment. Unless specific directions are followed, the manner of mixing the solids into water will vary with the user. This variation will affect how the solid components are juxtaposed and agitated in the suspension before dissolving, thereby allowing a variable reaction between the hypochlorite anion and the chlorite anion, and thereby affecting the course of both the competitive and desired reactions. Because of the unpredictable degree to which chlorite will participate in the competitive reaction and the consequent effect on the final concentration of chlorine dioxide solution prepared, the one bag method, while it allows preparation of satisfactory and usable chorine dioxide solutions, is not preferred for applications which require close control over the chlorine dioxide dosage.

In the invention herein disclosed in many instances precise amounts and ratios have been set forth, however some variances of the amounts and ratios are expected to yield effective results as readily understood by those skilled in the art.

Lithium hypochlorite has advantages over calcium hypochlorite. For example, calcium hypochlorite dissolves too slowly to serve as a source of a significant quantity of hypochlorous acid, and has an objectionably strong chlorine odor (lithium hypochlorite has very little chlorine odor) and when used with NaHSO$_4$ calcium hypochlorite forms solid calcium sulfate precipitate, resulting in low yields of chlorine dioxide with significant amounts of calcium sulfate solids impurity.

In its broadest sense, the herein disclosed invention embodies a product capable of being used for disinfection and/or oxidation comprising effective amounts of lithium hypochlorite, sodium bisulfate and sodium chlorite. Ideally, the lithium hypochlorite and sodium bisulfate are packaged together and the sodium chlorite is packaged alone. The product is supplied in the packages in substantially the following ratio:

NaClO$_2$=1.0

LiOCl=1.09

NaHSO$_4$=1.38

These ratios are of substantial amounts and can be varied as understood by those skilled in the art.

There is disclosed a method for preparing an active chlorine dioxide disinfecting solution comprising dissolving the contents of an Activator Pack containing LiOCl and NaHSO$_4$ in water and then shortly thereafter rapidly adding the Chlorite Pack containing NaClO$_2$ to said water containing therein the dissolved contents of the Activator Pack.

The active ingredients can be packaged in three individual packs.

The herein disclosed invention envisions methods for disinfecting a surface desired to be disinfected comprising applying to said surface the disclosed active ingredients added to water. In addition, fruits and vegetables can be disinfected, or waste water can be deodorized by the disclosed active ingredients added to water.

Many advantages accrue from applicant's invention:

1) Chlorine dioxide is generated with ease and in a predictable concentration.

2) No pre-mixing or measurement of ingredients is required.

3) Applications too small to justify a generator will find it convenient to employ the inventive composition.

4) No toxic or unpleasant organic residue accompanies the use of the inventive composition.

Obviously, many modifications may be made without departing from the basic spirit of the present invention. Accordingly, it will be appreciated by those skilled in the art that within the scope of the appended claims, the invention may be practiced other than has been specifically described herein, as for example three (3) packets of individual chemical ingredients,

What is claimed is:

1. A chlorine dioxide generating formulation which comprises lithium hypochlorite, sodium bisulfate, sodium chlorite and water, wherein the lithium hypochlorite, sodium bisulfate and sodium chlorite are present as dry components and water is added to the dry components to produce chlorine dioxide; the dry components being present substantially in a ratio of 1.09, 1.38 and 1.00, respectively.

2. The chlorine dioxide generating formulation of claim 1 wherein the lithium hypochlorite and sodium bisulfate are packaged together and the sodium chlorite is packaged alone.

3. The chlorine dioxide generating formulation of claim 1 wherein each of lithium hypochlorite, sodium bisulfate and sodium chlorite are packaged in individual packs.

4. The chlorine dioxide generating formulation of claim 2 wherein the lithium hypochlorite is present in substantially 6.12 g the sodium bisulfate is present in substantially 7.7 g and the sodium chlorite is present in substantially 5.6 g.

5. A method for preparing a chlorine dioxide solution comprising the steps of dissolving completely the contents of an Activator Packet containing lithium hypochlorite and sodium bisulfate in water and thereafter adding a Chlorite Packet containing sodium chlorite to said water containing therein the dissolved contents of the Activator Packet and wherein the ratio of ingredients is substantially 6.12 g lithium hypochlorite, substantially 7.7 g sodium bisulfate and substantially 5.6 g sodium chlorite.

6. A method of disinfecting to insure the potability of water comprising adding the chlorine dioxide generating formulation of claim 1 to drinking water.

7. A chlorine dioxide generating formulation contained within a one pack formulation to be added to water comprising in the following ratio: substantially 1.0 part of sodium chlorite; 0.97 part of lithium hypochlorite; and 1.22 part of sodium bisulfate.

8. A chlorine dioxide generating formulation comprising a one pack formulation containing substantially 6.16 g of lithium hypochlorite; 7.7 g of sodium bisulfate and 6.33 g of sodium chlorite to be added to a liter of water to produce substantially a 3000 ppm chlorine dioxide solution.

9. A method for preparing a composition which comprises substantially 3000 ppm of chlorine dioxide per liter comprising adding the chlorine dioxide generating formulation of claim 4 to a liter of water in an amount effective to disinfect said water.

10. A method for disinfecting a surface comprising applying to said surface the chlorine dioxide generating formulation of claim 1.

11. A method for disinfecting fruits and vegetables applying to the surface of said fruits and vegetables the chlorine dioxide generating formulation of claim 1.

12. A method of deodorization of waste water comprising exposing said waste water to the chlorine dioxide generating formulation of claim 1.

* * * * *